United States Patent [19]
Hiebl et al.

[11] Patent Number: 5,627,302

[45] Date of Patent: May 6, 1997

[54] ASYMMETRICALLY SUBSTITUTED DIAMINODICARBOXYLIC ACID DERIVATIVES

[75] Inventors: Johann Hiebl, Pichling; Franz Rovenszky, Linz, both of Australia

[73] Assignee: Hafslund Nycomed Pharma Aktiengesellschaft, Linz, Australia

[21] Appl. No.: 637,052

[22] Filed: Apr. 24, 1996

Related U.S. Application Data

[63] Continuation-in-part of Ser. No. 293,034, Aug. 19, 1994, abandoned.

[30] Foreign Application Priority Data

Aug. 20, 1993 [AU] Australia .................................. 1683/93

[51] Int. Cl.$^6$ .................................................. C07C 261/00
[52] U.S. Cl. ........................... 560/158; 560/21; 560/22; 560/27; 560/29; 560/30; 560/39; 560/41; 560/159; 560/169; 205/435
[58] Field of Search ............................ 560/21, 22, 27, 560/29, 30, 39, 41, 158, 159, 169

[56] References Cited

U.S. PATENT DOCUMENTS

| | | | |
|---|---|---|---|
| 4,161,521 | 7/1979 | Veber | 424/177 |
| 4,810,778 | 3/1989 | Callahan | 530/328 |
| 5,364,851 | 11/1994 | Joran | 530/345 |

OTHER PUBLICATIONS

R. Nutt et al., *J. Org. Chem.*, 45, 3078–3080 (1980).

Jurgens, *Tetrahedron Letters*, 33(33), 4727–4730 (1992) (abstract).

*Primary Examiner*—Michael L. Shippen
*Attorney, Agent, or Firm*—Wenderoth, Lind & Ponack

[57] ABSTRACT

The invention relates to novel asymmetrically substituted diaminodicarboxylic acid derivatives of the formula

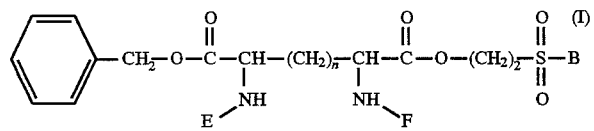

2 Claims, No Drawings

ASYMMETRICALLY SUBSTITUTED DIAMINODICARBOXYLIC ACID DERIVATIVES

This is a continuation-in-part of Ser. No. 08/293,034, filed Aug. 19, 1994, now abandoned.

The invention relates to novel asymmetrically substituted diaminodicarboxylic acid derivatives.

Asymmetrically substituted diaminodicarboxylic acid derivatives are useful intermediates for the synthesis of peptides.

In J. Org. Chem. 1980, 45, 3078–3080, asymmetrically substituted diaminosuberic acid derivatives are described which were prepared by mixed Kolbe synthesis. Separation from the symmetrical by-products was unsuccessful there because of very close polarities. The preparation of asymmetrically substituted diaminopimelic acid derivatives by a complicated 9-stage enantioselective synthesis is also known from Tetrahedron Lett. 30, 1992, 33, 4727–4730.

Unexpectedly, it has been possible to synthesize novel asymmetrically substituted diaminodicarboxylic acid derivatives which are easily separable from their symmetrically substituted reaction by-products. The compounds of the invention are useful intermediates for the synthesis of peptides and compounds containing unnatural amino acids.

The invention therefore relates to asymmetrically substituted diaminodicarboxylic acid derivatives of the formula

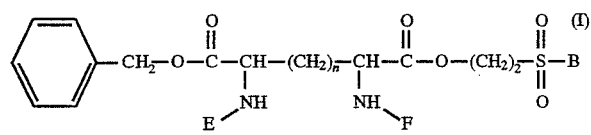

wherein

B represents methyl or phenyl,

E and F in each case represent an optionally halogenated straight chain, branched or cyclic alkyl radical having 1 to 10 C atoms or

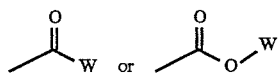

where W represents 9-fluorenylmethyl, benzyl which is optionally mono-, poly- or mixed substituted by halogen, —NO$_2$, alkoxy or —CN or W represents a straight chain or branched alkyl radical having 1 to 4 C atoms, and n represents an integer from 2 to 10.

The radicals E and F in each case represent an optionally halogenated straight-chain, branched or cyclic alkyl radical having 1–10 C atoms, for example a methyl, ethyl, n-propyl, i-propyl, n-butyl, i-butyl, t-butyl, pentyl or hexyl radical, which can optionally be mono- or polyhalogenated.

The radicals E and F can additionally represent a radical

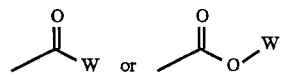

where W represents a 9-fluorenylmethyl radical or a benzyl radical which is optionally mono- or polysubstituted by halogen, NO$_2$, alkoxy or —CN or mixed radicals therefrom, for example a bromobenzyl, dibromobenzyl, chlorobenzyl, dichlorobenzyl, nitrobenzyl, methoxybenzyl or cyanobenzyl radical.

The radicals E and F preferably in each case represent a radical

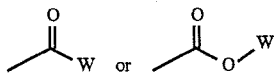

where W represents a 9-fluorenylmethyl radical, an optionally substituted benzyl radical or a straight-chain or branched alkyl radical having 1–4 C atoms. If the radicals A and B are different, the substituents on the amino function of the dicarboxylic acid can be identical or different. If the radicals A and B are identical, the substituents on the amino function of the dicarboxylic acid must be different.

The centers of chirality of the dicarboxylic acids are determined by the choice of the starting materials used. They can either both have the D configuration or both have the L or D,L or L,D configuration respectively, for example N'-E-N"-F-2,7-D,L-2,7-diaminosuberic acid mono-A ester mono-B ester when using N-E-D-glutamic acid A ester and N-F-L-glutamic acid B ester.

The asymmetrically substituted dicarboxylic acid derivatives according to the invention can be prepared by mixed Kolbe synthesis. In this process, appropriately protected amino acid derivatives are subjected to electrolysis on platinum wire-gauze electrodes.

The starting compounds are known from the literature or can be prepared by methods familiar to the person skilled in the art.

The amino acid derivatives are dissolved in a solvent which is inert under the reaction conditions. Suitable solvents are, for example, lower aliphatic alcohols, for example methanol, ethanol, propanol or i-propanol or a heterocyclic solvent such as, for example, pyridine, or dimethylformamide, acetonitrile, nitromethane or mixtures of such solvents.

In the electrolysis cell the solution of a base is added, for example alkali metal in alcoholic solution, for example sodium methoxide in methanol, or potassium ethoxide in ethanol. Electrolysis is then carried out on platinum wire-gauze electrodes with cooling, the temperature preferably being kept at 18°–25° C. The current strength during the electrolysis is about 5–15 A at 60–120 V applied voltage and depends on the geometry of the electrodes used.

The electrolysis process is complete as soon as starting material can no longer be determined in the electrolysis solution.

The electrolysis solution is then optionally concentrated under low pressure, the residue is taken up in a suitable solvent, for example ethyl acetate, and this solution is washed successively with dilute acid, for example dilute hydrochloric acid, a saturated salt solution, for example a saturated sodium hydrogen carbonate solution, and saturated sodium chloride solution.

The solution is then dried with a suitable drying agent, for example sodium sulfate or magnesium sulfate, filtered and concentrated again, optionally under low pressure.

The residue is purified by chromatography, for example on silica gel, it being possible to separate the symmetrically substituted by-products. The reaction proceeds in a good yield of 10–15% of theory to give the desired asymmetrically substituted final product.

EXAMPLE 1

28.34 g (84 mmol) of α-benzyl-N-t-butoxycarbonylglutamate and 37.76 g (84 mmol) of α-(2-tosylethyl)-N-benzyloxycarbonylglutamate were dissolved in a mixture of 240 ml of MeOH and 80 ml of pyridine. The reaction solution was transferred to the electrolysis cell having cylindrically arranged platinum wire-gauze electrodes. It was rinsed with MeOH and the electrolysis cell filled with MeOH until both electrodes were completely immersed.

0.8 ml of $NaOCH_3$ (30% in MeOH) were then added, and the 25 electrolysis cell was well cooled. When the reaction solution has cooled to 15° C., the reaction was started. The reaction temperature was kept between +18° and +24° C. by temperature control or by control of the current strength or current potential (5–15 A, 60–120 V).

The reaction course was checked by means of TLC.

After complete reaction the reaction solution was concentrated in a rotary evaporator at 40° C.

The residue from the Kolbe synthesis was dissolved in 500 ml of ethyl acetate, and washed first with dilute HCl solution (25 ml of conc. HCl made up to 250 ml with $H_2O$), then with 250 ml of sat. $NaHCO_3$ and finally with 250 ml each of sat. NaCl up to neutrality of the aqueous phase.

The organic phase was dried with $Na_2SO_4$, filtered off and evaporated.

Evaporation residue: 56.2 g.

The evaporation residue was filtered through silica gel and then separated by means of HPLC.

Yield: 6.4 g of pure α-benzyl-α'-(2-tosylethyl)-N(α')-benzyloxycarbonyl-N(α)-t-butyloxycarbonyl-2,7-diaminosuberate (11% of theory), Oil, $[a]_D$=+3.45° (3% in $CHCl_3$).

The following compounds were prepared in an analogous manner:

| No. | A | B | E | F | n |
|---|---|---|---|---|---|
| 2 | O-Benzyl | O-2-Tosylethyl | t-Butyloxycarbonyl | t-Butyloxycarbonyl | 4 |
| 3 | O-Benzyl | O-2-Tosylethyl | t-Butyloxycarbonyl | Benzyloxycarbonyl | 3 |
| 4 | O-Benzyl | O-2-Tosylethyl | t-Butyloxycarbonyl | Benzyloxycarbonyl | 2 |
| 5 | O-Benzyl | O-2-Tosylethyl | t-Butyloxycarbonyl | Benzyloxycarbonyl | 3 |

In Examples 3 and 5 the corresponding D- and L-amino acid derivatives were employed in mixed form.

Chemical data of the above mentioned compounds, where the abbreviations used have the following meaning:

| Abbreviation | Meaning |
|---|---|
| OBn | O-benzyl |
| OEtTos | O-(2-tosylethyl) |
| OtBu | O-t-butyl |
| Boc | t-butyloxycarbonyl |
| Z | benzyloxycarbonyl |
| SUB | n = 4 |
| PIM | n = 3 |
| ADI | n = 2 |

EXAMPLE 1

Boc-Z-SUB-OBn-OEtTos $C(CDCl_3,100 MHz)$:21.65Tolyl-$CH_3$), 24.65($CH_2$), 24.81 ($CH_2$), 28.32(($CH_3$)$_3$C), 32.06($CH_2$),32.38($CH_2$),53.12(CH) ,53.80(CH),54.94(O$CH_2CH_2SO_2C_7H_7$), 58.27 (O$CH_2CH_2SO_2C_7H_7$),67.01(benzyl-$CH_2$),67.17(benzyl-$CH_2$),80.05(($CH_3$)$_3$C), 128.12–128.65(aromatic C),130.08, 135.32,136.27,145.23,155.26 and 155.90(carbamate CO), 172.15(2 ester CO)

Oil $[α]$=+3.45 (5% in $CHCl_3$)

EXAMPLE 2

Di-Boc-D,L-SUB-OBn-OEtTos $C(CDCl_3,100 MHz)$:21.63(tolyl-$CH_3$),24.79($CH_2$),24.84 ($CH_2$),28.31(2($CH_3$)$_3$ C), 32.13($CH_2$),32.52($CH_2$),53.23(br s, 2CH),54.99(O$CH_2CH_2SO_2C_7H_7$), 58.28 (O$CH_2CH_2SO_2C_7H_7$),67.01(benzyl-$CH_2$),79.98(2($CH_3$)$_3$C), 128.13–128.61(aromatic C),135.45,136.35,145.21, 155.30 and 155.83(carbamate CO), 172.11(2 ester CO)

EXAMPLE 3

Boc-Z-PIM-OBn-OEtTos $C(CDCl_3,100 MHz)$:21.10($CH_2$),21.60(tolyl-$CH_3$),28.31( ($CH_3$)$_3$ C),31.62($CH_2$), 31.90($CH_2$),52.85(CH),53.55(CH), 54.93(O$CH_2CH_2SO_2C_7H_7$), 58.32(O$CH_2CH_2SO_2C_7H_7$), 67.05 and 67.22(benzyl-$CH_2$),80.08(($CH_3$)$_3$C), 128.11–128.66(aromatic C),130.05,135.31,136.25,145.21, 155.45 and 155.83(carbamate CO), 171.97 and 172.08(ester CO)

EXAMPLE 4

Boc-Z-ADI-OBn-OEtTos $C(CDCl_3,100 MHz)$:21.60(tolyl-$CH_3$),28.17(($CH_3$)$_3$C), 28.29($CH_2$),52.79(CH), 53.61 (CH),54.87 (O$CH_2CH_2SO_2C_7H_7$),67.04 and 67.31(benzyl-$CH_2$),80.18( ($CH_3$)$_3$C),128.05–128.67(aromatic C),130.09,135.24, 136.20,136.26,145.27 and 156.00(2 carbamate CO),171.59 and 171.75(ester CO)

EXAMPLE 5

Boc-Z-D,L-PIM-OBn-OEtTos $C(CDCl_3,100 MHz)$:20.98($CH_2$),21.58(tolyl $CH_3$),28.29( ($CH_3$)$_3$ C),31.77($CH_2$), 31.93($CH_2$),52.98(CH),53.73(CH), 54.94(O$CH_2CH_2SO_2$ $C_7H_7$), 58.25(O$CH_2CH_2SO_2C_7H_7$), 67.00 and 67.15(benzyl-$CH_2$),80.10(($CH_3$)$_3$C), 128.09–128.64(aromatic C),130.05,135.31,136.32,145.19, 155.28 and 156.02(carbamate CO), 171.87 and 171.94 (ester CO).

What we claim is:

1. An asymmetrically substituted diaminodicarboxylic acid derivative of the formula

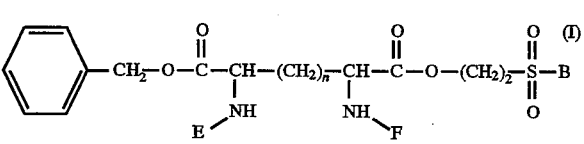

wherein

B represents methyl or phenyl,

E and F in each case represent an optionally halogenated straight chain, branched or cyclic alkyl radical having 1 to 10 C atoms or

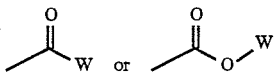

where W represents 9-fluorenylmethyl, benzyl which is optionally mono-, poly- or mixed substituted by halogen, —NO$_2$, alkoxy or —CN or W represents a straight chain or branched alkyl radical having 1 to 4 C atoms, and n represents an integer from 2 to 10.

2. An asymmetrically substituted diaminodicarboxylic acid derivative of the formula I according to claim 1, wherein E and F in each case represent

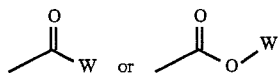

where W represents 9-fluorenylmethyl, benzyl which is optionally mono-, poly- or mixed substituted by halogen, —NO$_2$, alkoxy or —CN or W represents a straight chain or branched alkyl radical having 1 to 4 C atoms.

* * * * *